United States Patent [19]
Miller

[11] Patent Number: 6,166,282
[45] Date of Patent: Dec. 26, 2000

[54] FAST-FLUIDIZED BED REACTOR FOR MTO PROCESS

[75] Inventor: Lawrence W. Miller, Palatine, Ill.

[73] Assignee: UOP LLC, Des Plaines, Ill.

[21] Appl. No.: 09/378,416

[22] Filed: Aug. 20, 1999

[51] Int. Cl.[7] .............................. C07C 1/00; F27B 15/00; F27B 15/08

[52] U.S. Cl. ........................ 585/638; 585/639; 585/640; 585/641; 585/642; 422/141; 422/142; 422/143; 422/144; 422/145; 422/147

[58] Field of Search ..................... 585/639, 638, 585/640, 641, 642; 422/141, 142, 143, 144, 145, 147

[56] References Cited

U.S. PATENT DOCUMENTS

| | | | |
|---|---|---|---|
| 3,928,483 | 12/1975 | Chang et al. | 260/668 R |
| 4,025,575 | 5/1977 | Chang et al. | 260/682 |
| 4,252,479 | 2/1981 | Scherfenberg | 406/182 |
| 4,328,384 | 5/1982 | Daviduk et al. | 585/469 |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,499,327 | 2/1985 | Kaiser | 585/640 |
| 4,547,616 | 10/1985 | Avidan et al. | 585/640 |
| 4,677,242 | 6/1987 | Kaiser | 585/638 |
| 4,677,243 | 6/1987 | Kaiser | 585/638 |
| 4,843,183 | 6/1989 | Inui | 585/640 |
| 4,849,091 | 7/1989 | Cabrera et al. | 208/113 |
| 4,861,938 | 8/1989 | Lewis et al. | 585/640 |
| 4,873,390 | 10/1989 | Lewis et al. | 585/638 |
| 4,929,780 | 5/1990 | Wright et al. | 585/303 |
| 4,973,792 | 11/1990 | Lewis et al. | 585/638 |
| 5,095,163 | 3/1992 | Barger | 585/640 |
| 5,126,308 | 6/1992 | Barger et al. | 502/214 |
| 5,177,279 | 1/1993 | Harandi | 585/312 |
| 5,191,141 | 3/1993 | Barger et al. | 585/640 |

FOREIGN PATENT DOCUMENTS

WO 99/01219  1/1999  WIPO.

*Primary Examiner*—Marian C. Knode
*Assistant Examiner*—Thuan D. Dang
*Attorney, Agent, or Firm*—John G. Tolomei; Frank S. Molinaro; Richard P. Silverman

[57] ABSTRACT

An oxygenate conversion process and fast-fluidized bed reactor are disclosed having an upper disengaging zone and a lower reaction zone. The process is carried out in a reaction zone having a dense phase zone in the lower reaction zone and a transition zone which extends into the disengaging zone. The feedstock in the presence of a diluent is passed to the dense phase zone containing a non-zeolitic catalyst to effect at least a partial conversion to light olefins and then passed to the transition zone above the dense phase zone to achieve essentially complete conversion. A portion of the catalyst is withdrawn from above the transition zone in the disengaging zone, at least partially regenerated, and returned to a point above the dense phase zone, while catalyst is continuously circulated from the disengaging zone to the lower reaction zone. The process includes a first separation zone in the disengaging zone between the transition zone and at least one cyclone separation stage to separate catalyst from the reaction product. The process and apparatus provide a method for carrying out the overall conversion reaction with a significantly reduced catalyst inventory compared to conventional bubbling bed reactors.

15 Claims, 1 Drawing Sheet

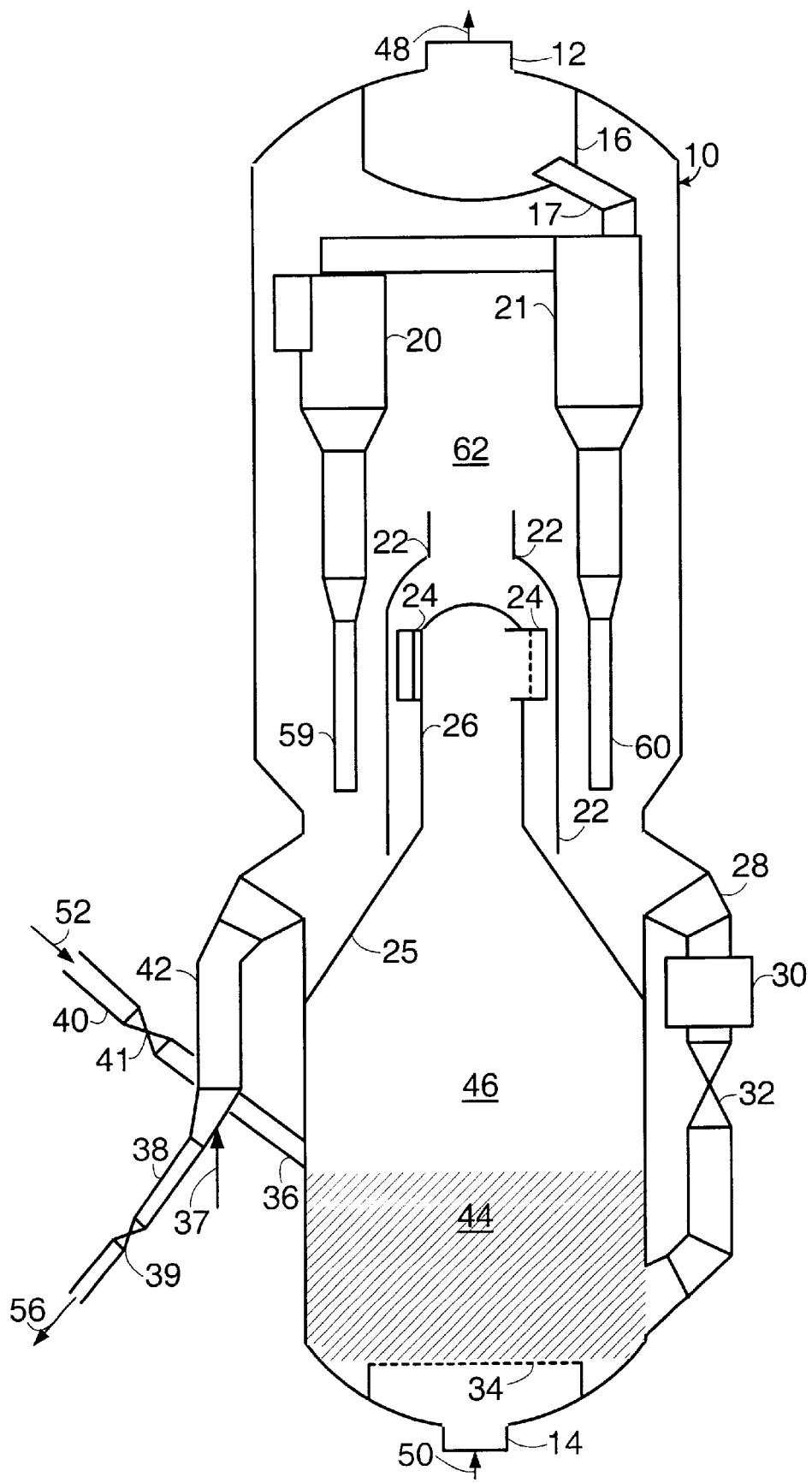

FAST-FLUIDIZED BED REACTOR FOR MTO PROCESS

FIELD OF THE INVENTION

The present invention relates generally to hydrocarbon conversion processes utilizing a fluidized bed reaction zone. More particularly, the present invention relates to a process and a reactor for use in the conversion of methanol to olefins where light olefins are desired products.

BACKGROUND OF THE INVENTION

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483; 4,025,575 and 4,252,479 (Chang et al.); 4,496,786 (Santilli et al.); 4,547,616 (Avidan et al.); 4,677,243 Kaiser); 4,843,183 (Inui); 4,499,314 (Seddon et al.); 4,447,669 (Harmon et al.); 5,095,163 (Barger); 5,191,141 (Barger); 5,126,308 (Barger); 4,973,792 (Lewis); and 15 4,861,938 (Lewis).

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include, but are not limited to, helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene. The above U.S. patents are hereby incorporated by reference.

U.S. Pat. No. 4,499,327 (Kaiser) discloses a process for the production of light olefins from a feedstream comprising methanol, ethanol, dimethylether, diethylether, or mixtures thereof, comprising contacting the feedstream with a silicoaluminophosphate molecular sieve at effective process conditions to produce light olefins.

U.S. Pat. No. 4,849,091 discloses a two-stage regeneration arrangement for use in a fluidized catalytic cracking system providing initial coke combustion below catalyst in a low catalyst density, high efficiency contact zone followed by substantial separation of catalyst and regeneration gas and complete regeneration of catalyst particles in a dense bed regeneration zone. Catalyst and gas flow co-currently prior to this separation but flow counter-currently after the separation.

World Patent Application WO 99/01219 discloses a method for selectively converting oxygenates to light olefins in which desirable carbonaceous deposits are maintained on the total reaction volume of catalyst by regenerating only a portion of the total reaction volume of catalyst and mixing the regenerated portion with the unregenerated total reaction volume of catalyst. The method incorporates a fluidized bed reactor with continuous regeneration. In a preferred arrangement, the oxygenate feed is mixed with regenerated catalyst and coked catalyst at the bottom of a riser and the mixture is lifted to a disengaging zone. In the disengaging zone, coked catalyst is separated from the gaseous materials by means of gravity or cyclone separators. A portion of the coked catalyst to be regenerated is sent to a stripping zone to recover adsorbed hydrocarbons. Stripped spent catalyst is passed to a regenerator.

U.S. Pat. No. 4,547,616 discloses an improvement in a process for the conversion of oxygenate or alcohols to olefins by the operation of a fluidized bed in a turbulent fluidization regime at elevated temperatures and controlled catalyst activity. It is disclosed that the fluidized catalyst bed is maintained in a vertical reactor column having a turbulent reaction zone to achieve good mixing at a velocity greater than the dense bed transition velocity to a turbulent regime and less than transport velocity for the average catalyst particle. The superficial fluid velocity is disclosed in a range between about 0.3 to 2 meters per second. Provision is made for passing partially regenerated catalyst to the reactor fluidized bed of catalyst beneath the upper interface and sufficiently below to achieve good mixing in the fluid bed. It is further disclosed that the bed of catalyst in the reactor can be least 5 to 20 meters in height, preferably about 9 meters.

U.S. Pat. No. 4,328,384 discloses a process for the conversion of alcohols and related oxygenates in a riser reactor and a dense fluid catalyst bed wherein the catalyst is circulated through a plurality of satellite stripping-cooling zones for temperature control. The process comprises passing a suspension of vaporized reacted material and fluid catalyst particles comprising a zeolite material upwardly through a relatively disbursed catalyst riser followed by passing the suspension comprising products of reaction upwardly through a relatively dense fluid mass of catalyst particles with an extended residence time in order to achieve total conversion of the oxygenate. Catalyst is withdrawn from a lower portion of the relatively dense bed of catalyst particles and passed downwardly through a plurality of separate catalyst stripping-cooling zones prior to being returned to the riser reactor. Stripped products are removed from the stripping- cooling zones wherein products are separated above a more dense fluid mass of catalyst than in the separate catalyst stripping-cooling zones.

U.S. Pat. No. 4,873,390 (Lewis et al.) discloses a process for catalytically converting a feedstream, e.g., an aliphatic hetero compound, such as methanol, into a product, e.g., light olefins, wherein the conversion to olefins can be selectively enhanced as compared to the conversion to paraffins by employing a catalyst that is not completely regenerated, i.e., contains a desired quantity of carbonaceous material.

U.S. Pat. No. 4,929,780 (Wright et al.) discloses an integrated process of converting methanol and other lower molecular weights oxygenates to gasoline, distillate range liquid hydrocarbons, and ethylene. The patent discloses the use of a fixed bed reactor in conjunction with a fluidized bed reactor in order to increase the yield to ethylene.

In view of the sensitivity of many of the above-described hydrocarbon conversion processes to reaction variables such as temperature, catalytic activity, and space velocity, improved processes are sought for controlling the process in order to obtain desired conversion products while inhibiting the conversion to by-products. More specifically, improved fluidized bed hydrocarbon conversion processes are sought which require lower catalyst inventories, simplify operation, and provide a sufficient amount of active catalyst sites in order to enhance the conversion to the desired products without enhancing the conversion to by-products.

SUMMARY OF THE INVENTION

The apparatus of the present invention comprises a fast-fluidized bed reactor for carrying out an oxygenate conversion reaction with a significantly reduced catalyst inventory compared to traditional bubbling bed reactors. By employing both a dense phase zone and a transition zone in the same reactor, combined with an initial catalyst separation or disengagement step, significant advantages over the traditional bubbling bed reactors can be obtained. Traditional bubbling bed reactors of the type employed in fluid catalytic cracking provide good contact between the feedstock and the catalyst bed and provide a regime wherein the activity of the overall catalyst bed can be maintained by the periodic or continuous regeneration of a portion of the catalyst bed. Generally, these bubbling bed reactors operate at superficial velocities less than about 1 meter per second (3 feet per second) and, as a result, require the diameter and hence the volume of the bubbling bed to be very large. Although good mixing is attainable, the resulting catalyst inventory is large and the responsiveness of the process to changes in feedstock quality is slow, making heat removal from the reaction zone more critical. Unlike fluid catalytic cracking, the oxygenate conversion process is exothermic and the selectivity is dependent upon the activity of the catalyst which is quickly deactivated. By the use of a fast-fluidized bed reactor of the present invention, the cross-sectional area of the reactor can be reduced from 1 to 8 times over a bubbling bed. Coupled with an initial catalyst disengagement step to provide an initial catalyst separation from the reactor product vapor, the number of cyclone stages and the diameter of the upper disengagement zone or upper reactor zone can be reduced. The combination of the fast-fluidized bed reactor with a lower dense phase zone and an upper transition phase zone, and the initial catalyst separation provides significant capital cost reduction, results in improved operational stability, and makes heat removal from the reactor more manageable. The process includes the return of the regenerated catalyst at a point above the dense phase zone which improves selectivity.

In one embodiment, the present invention is a process for the conversion of a feedstream comprising an oxygenate to produce light olefins. The process comprises a series of steps. The feedstream in the presence of a diluent and at effective conditions is passed to a dense phase zone in a lower reaction zone of a fast-fluidized bed reactor. The reactor contains a fluidized non-zeolitic catalyst. In the dense phase zone, the feedstream is at least partially converted to a product stream comprising light olefins. Associated with the reaction, at least a portion of the catalyst is deactivated to produce a spent catalyst which has a carbonaceous deposit thereon. The product stream, an unconverted portion of the feedstream, a catalyst mixture comprising spent catalyst, and a regenerated catalyst are passed to a transition phase zone located in the lower reaction zone above the dense phase zone. In the transition zone, the unconverted portion of the feedstream is essentially completely converted to produce a transition zone effluent comprising light olefins and the catalyst mixture. The transition zone effluent is passed to a first separation zone in a disengaging zone to separate a first portion of the catalyst mixture and to provide a first separated product stream comprising the catalyst mixture. The first portion of the catalyst mixture is passed to an upper catalyst bed in the disengaging zone. The first separated product stream is passed to a second separation zone to provide a net product stream comprising a reduced amount of the catalyst mixture relative to the product stream. A second portion of the catalyst mixture is returned to the upper catalyst bed. At least a portion of the catalyst mixture from the upper catalyst bed is returned to the dense phase zone. A third portion of the catalyst mixture is withdrawn from the upper catalyst bed and at least partially regenerated to provide a regenerated catalyst. The regenerated catalyst is returned to the lower reaction zone at a point above the dense phase zone to decrease catalyst inventory.

In another embodiment, the present invention is a fast-fluidized bed reactor for the conversion of a feedstream comprising an oxygenate by contact with fluidized catalyst particles to produce a product stream comprising light olefins. The fast-fluidized bed reactor comprises a reaction vessel which defines a disengaging zone, a lower subadjacent reaction zone, a product outlet for withdrawing the product stream from the disengaging zone, and a feed inlet communicating with the lower reaction zone. A partition is sealingly disposed about an intermediate portion of the reaction vessel to segregate the reaction zone from the disengaging zone. A riser extends vertically from the reaction zone into a central section of the disengaging zone. The riser is in fluid communication with the reaction zone for conducting the product stream and fluidized catalyst particles. A discharge opening is defined within the disengaging zone for discharging the product stream and fluidized catalyst particles. The discharge opening is tangentially oriented for imparting a tangential velocity to the product stream and fluidized catalyst particles. A separation vessel is disposed over the riser in the disengaging zone. The separation vessel surrounds the discharge opening to separate gaseous products from fluidized catalyst particles. The separation vessel has lower portion defining a particle outlet for discharging fluidized catalyst particles and defines a gas recovery outlet for discharging gaseous fluids from the separation vessel. A dense phase zone is defined by a portion of the reaction zone located below the intermediate portion of the reaction zone. At least one catalyst recirculation standpipe is provided for conveying fluidized catalyst particles from the disengaging zone to the dense phase zone. A spent catalyst standpipe is provided in fluid communication with the reaction zone for removing catalyst particles from the disengaging zone. A regenerated catalyst standpipe is provided in fluid communication with the disengaging zone for delivering regenerated catalyst particles to the intermediate portion of the reaction zone.

BRIEF DESCRIPTION OF THE DRAWING

The drawing is a schematic diagram of a fast-fluidized bed reactor for use in the present invention.

DETAILED DESCRIPTION OF THE INVENTION

Aliphatic hetero compounds are particularly preferred feedstreams for use in the present invention, especially when light olefins, i.e., olefins containing 2 to about 6 and preferably 2 to 4 carbon atoms per molecule are to be produced. The term "aliphatic hetero compounds" is employed herein to include alcohols, halides, mercaptans, sulfides, amines, ethers and carbonyl compounds, e.g., aldehydes, ketones, carboxylic acids and the like. The aliphatic moiety preferably contains from 1 to about 10 carbon atoms, and more preferably from about 1 to 4 carbon atoms. Examples of suitable aliphatic hetero compounds include: methanol, methyl mercaptan, methyl sulfide, methyl amine, dimethyl ether, ethanol, ethyl mercaptan, ethyl chloride, diethyl ether, methylethyl ether, formaldehyde, dimethyl ketone, acetic acid, alkyl amines, alkyl halides, and alkyl sulfides. In the aspect of the invention where light olefins and/or gasoline range hydrocarbons are the desired products, the feedstream is preferably selected from methanol, ethanol, dimethyl ether, diethyl ether, and mixtures thereof, with methanol being particularly preferred.

The product or products obtained from the conversion process will, of course, depend, for example, on the feedstream, catalyst and conditions employed. Preferably, the desired product is organic. The organic product or products are preferably hydrocarbons in the C2 to C6 carbon range. In one aspect, the desired product preferably contains light olefins having from about 2 to 6, more preferably from about 2 to 4 carbon atoms per molecule. The desired product or products preferably have kinetic diameters which allow such product or products to be removed from or escape from the pores of the catalyst.

Reaction conditions for the conversion of aliphatic hetero compounds can be determined by those skilled in the art and preferably, in accordance with the present invention, comprise a temperature of from about 200° to 600° C., more preferably from about 300° to 500° C., and a pressure of from about 1 to 200 psia, more preferably from about 20 to 100 psia. Typical processes for producing light olefins are described in U.S. Pat. Nos. 4,499,327 and 4,873,390 cited above and hereby incorporated by reference.

A diluent is required to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons (e.g., methane), aromatic hydrocarbons (e.g., benzene, toluene), and mixtures thereof. The amount of diluent used can vary considerably and is usually from about 5 to about 90 mole percent of the feedstock and preferably from about 25 to about 75 mole percent. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to about 0.1 to 5 moles of water have been disclosed.

Non-zeolitic molecular sieves include molecular sieves which have the proper effective pore size and are embraced by an empirical chemical composition, on an anhydrous basis, expressed by the empirical formula:

(ELxAlyPz)O2 where EL is an element selected from the group consisting of silicon, magnesium, zinc, iron, cobalt, nickel, manganese, chromium, and mixtures thereof, x is the mole fraction of EL and is at least 0.005, y is the mole fraction of Al and is at least 0.01, z is the mole fraction of P and is at least 0.01 and x+y+z=1. When EL is a mixture of elements, x represents the total amount of the metal mixture present. Preferred elements (EL) are silicon, magnesium, and cobalt with silicon being especially preferred. The preparation of various ELAPOs is well known in the art and may be found in U.S. Pat. Nos. 5,191,141 (ELAPO); 4,554,143 (FeAPO); 4,440,871 (SAPO); 4,853,197 (MAPO, MnAPO, ZnAPO, CoAPO); 4,793,984 (CAPO), 4,752,651 and 4,310,440 all of which are incorporated by reference.

An especially preferred embodiment is one in which EL is silicon (usually referred to as SAPO). The SAPOs which can be used in the instant invention are any of those described in U.S. Pat. Nos. 4,440,871, 5,126,308, and 5,191, 141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 angstroms. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 angstroms and less than about 5.0 angstroms.

The preferred catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength and the like, to the solid particles. Such matrix materials are often to some extent porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these, and the like.

If matrix materials, e.g., binder and/or filler materials, are included in the 10 catalyst composition, the non-zeolitic and/or zeolitic molecular sieves preferably comprise about 1 to 99 percent, more preferably about 5 to about 90 percent, and still more preferably about 10 to about 80 percent by weight of the total composition. The preparation of solid particles comprising catalyst and matrix materials is conventional and well known in the art and, therefore, need not be discussed in detail herein.

The operating conditions suitable for use in accordance with present invention depend, of course, on a particular conversion process and can be readily determined by those skilled in the art. Typical reaction parameters which control the reaction severity include temperature, space velocity, catalyst activity, and pressure. In general, reaction severity increases with increasing temperature, increasing catalyst activity, and decreasing space velocity. The effect of pressure on the reaction severity depends upon the particular reaction. Although in accordance with the present invention any of the above described variables can be adjusted as necessary in order to obtain the desired hydrocarbon conversion, the present invention is particularly directed to the catalyst activity, and more specifically directed to providing an effective amount of active catalyst sites within the moving bed reaction zone in order to enhance the conversion to desired products while not enhancing the conversion to undesired by-products.

During the conversion, a carbonaceous material, i.e., coke, is deposited on the catalyst as it moved downward through the reaction zone. The carbonaceous deposit material has the effect of reducing the number of active sites on the catalyst which thereby effects the extent of the conversion. Thus, during the fluidized bed conversion process, a portion of the coked catalyst is withdrawn from the reaction zone and regenerated to remove at least a portion of the carbonaceous material. Preferably, the carbonaceous material is removed from the catalyst by oxidative regeneration wherein the catalyst which is withdrawn from the reactor is contacted with an oxygen-containing gas at sufficient temperature and oxygen concentration to allow the desired amount of the carbonaceous materials to be removed from the catalyst.

Depending upon the particular catalyst and conversion, it can be desirable to substantially remove the carbonaceous material, e.g., to less than 1 weight percent, or only partially regenerate the catalyst, e.g., to from about 2 to 30 weight percent carbon. Preferably, the regenerated catalyst will contain about 0 to 20 percent and more preferably from about 0 to 10 percent carbon. Additionally, during regeneration, there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. It is preferred in most instances when relatively large concentrations of carbonaceous material are present on the catalyst, that is, greater than about 1 weight percent carbonaceous material on the catalyst, to cause the carbon burn-off to occur with an oxygen-containing gas stream. The details concerning the conditions for regeneration are known to those skilled in the art and need not be further disclosed herein. The regeneration zone is preferably configured as a fluidized bed zone similar to the reaction zone wherein the coked catalyst is fed to the regeneration zone wherein the carbonaceous material is removed and the regenerated catalyst is withdrawn from a lower section of the regeneration zone and recirculated to the reaction zone.

In accordance with the present invention, the catalyst, after being regenerated to remove carbonaceous deposit material and thereby increase the amount of active catalyst sites, is added above a dense phase zone in the lower reaction zone for further contacting with the feedstream. The rate of addition is selected so that a sufficient quantity of active catalyst sites are provided within the fluidized lower reaction zone in order to enhance the conversion of the feedstream to the desired products without enhancing the conversion to undesired by-products. Thus, if the by-products are formed by the continued conversion of the desired products which are in contact with active catalyst sites, then the rate of the addition of regenerated catalyst is decreased in accordance with the present invention in order to decrease the reaction rates. On the other hand, if the by-products are comprised of feed reactants or intermediate products, then the rate of addition of regenerated catalysts in accordance with the present invention is increased in order to increase the reaction rate and form the desired products. Preferably, the rate of addition is selected to provide at least 70 percent conversion, more preferably at least 90 percent conversion to the desired product and less than 30 percent conversion, more preferably less than 10 percent conversion to the by-product.

The present invention employs a fast-fluidized bed reactor which comprises an upper disengaging zone and a lower reaction zone. The lower reaction zone comprises a dense phase zone which operates within a superficial velocity range less than about 1 meter per second (3 feet per second). By the term "superficial velocity", it is meant the velocity of the gas as it flows through the vessel. The superficial velocity is typically determined by dividing the volumetric flow rate of the gas by the cross-sectional area of the vessel. A transition phase zone is disposed above the dense phase zone and extends from the lower reaction zone into the upper disengaging zone. The transition phase zone includes a reducing cone which reduces the flow path diameter from the diameter of the dense phase zone to the diameter of the riser. The superficial velocity within the transition zone ranges between about 1 meter per second (3 feet per second) and about 4 meters per second (13 feet per second). Feedstock at effective conditions is introduced into the lower reaction zone wherein it is contacted with a partially coked catalyst to selectively produce light olefins. As the unreacted feedstock and reaction products pass through the dense phase zone, they are carried into the transition zone with partially coked catalyst particles having a reduced number of active catalyst sites. As the mixture of unreacted feedstock, fluidized catalyst particles, and reaction products enters the transition zone, the reaction continues to essentially complete conversion (~99+mole percent) of the oxygenate feedstock. At lease one catalyst recirculation standpipe is provided to transfer or return a portion of the catalyst mixture from the upper catalyst bed to the dense phase zone. Preferably, at least one catalyst cooler is disposed in the catalyst recirculation standpipe to cool the catalyst mixture prior to returning the catalyst mixture to the dense phase zone. Preferably, the reaction zone comprises at least three catalyst recirculation standpipes and at least one of the recirculation standpipes includes a catalyst cooler to generate steam and cool the catalyst mixture. A portion of the catalyst from the dense phase zone is withdrawn, stripped in a conventional manner, and passed to a regeneration zone. In the regeneration zone, the coked catalyst is at least partially regenerated to produce a regenerated catalyst. The regenerated catalyst is returned to the reaction zone at a point above the dense phase zone. More particularly, the regenerated catalyst may be returned to the reaction zone at a point above the dense bed such as at a point in the riser or transition zone, or at a point in the disengaging zone such as to the upper catalyst bed. It is believed that by returning the regenerated catalyst to a point above the dense phase zone, contact between the freshly regenerated catalyst and the oxygenate feedstock is minimized, thereby improving selectivity to ethylene and the overall production of coke is reduced. The regenerated catalyst is lifted to the reaction zone with a portion of the net product stream. Preferably, the portion of the net product stream used to lift the regenerated catalyst comprises butene which was fractionated from the net product stream in a fractionation zone producing an ethylene stream, a propylene stream and a butylene stream.

The invention is hereinafter described with reference to the Example and the Drawing. Such description is intended for illustrative purposes and is not intended to limit the scope of the claims that follow.

DETAILED DESCRIPTION OF THE DRAWING

Referring to the drawing, a fast-fluidized bed reactor 10 for the production of light olefins from oxygenates is illustrated in schematic form. The fast-fluidized bed reactor comprises a disengaging zone 62 and a lower reaction zone consisting of a dense phase zone 44 and a transition phase zone 46. An oxygenate feedstock selected from the group consisting of methanol, ethanol, dimethyl ether, and the like is passed via line 50 to the feed inlet 14 in the presence of a diluent. The feedstock and diluent admixture passes through a feed distributor 34 and enters the dense phase zone 44. The feed distributor 34 consists of a uniformly flat sieve plate which permits the vapor phase feed admixture to pass through while retaining a catalyst above the sieve plate.

Generally, the feed distributor 34 is supported by a ring having an overall diameter smaller than the outside diameter of the generally circular feed distributor. A plurality of legs is disposed on the base of the reactor to support the ring. The legs are typically welded to the ring at right angles to the sieve plate to form a feed distributor assembly and the feed distributor assembly is rigidly disposed on the base of the lower reaction zone above the feed inlet 14. The ring serves to support the catalyst bed and to reduce vibrations in the feed distributor 34. The catalyst in the dense phase zone 44 and the transition phase zone 46 comprises a non-zeolitic small pore catalyst such as SAPO-34, SAPO-17, and mixtures thereof. As the feedstock enters the dense phase zone 44, the feedstock contacts the non-zeolitic small pore catalyst and reacts at effective conditions to produce a reaction product stream. The reaction product stream comprises light olefins, including ethylene, propylene, and butylene. In the course of the reaction, a carbonaceous deposit is produced on the catalyst, reducing the activity of the catalyst. The reaction product stream and a catalyst mixture comprising active catalyst and some deactivated catalyst are conveyed into the transition phase zone 46 in an intermediate portion of the reaction zone. As the reaction product and the catalyst mixture continue moving upwardly through the lower reaction zone into a riser section 26, the cross-sectional area of the flow path through the fast-fluidized bed reactor is reduced from the cross-sectional area of the dense phase zone 44 by a reducing means 25, or cone section, to the cross-sectional area of the riser section 26. In the fast-fluidized bed reaction system, the superficial velocity through the transition phase zone 46 varies between about 1 and 3 meters per second (about 3 to about 10 feet per second). The riser section 26 has a smaller diameter and a smaller cross-sectional area than the dense phase zone 44 which increases the superficial velocity through the riser relative to the dense phase zone 44. Because the superficial velocities in the riser section 26 are higher for the same feed rate, the cross-sectional area of the overall reactor zone can be decreased by about a factor of 2 or 3 times compared to the cross-sectional area of a bubbling bed reactor. In addition, the fast-fluidized bed reaction zone provides more precise control of the feedstock and catalyst rates without the need for external catalyst addition or removal. As a result, the fast-fluidized bed reaction system provides significantly decreased catalyst inventories over a bubbling bed reactor. The reaction product stream and catalyst mixture continue to be conveyed through the riser section. The riser section discharges the reaction product stream and catalyst mixture through a separation zone consisting of distributor arms 24, or discharge opening, and a separation vessel 22. The discharge opening 24 tangentially discharges the reaction product stream and catalyst mixture to create a centripetal acceleration of the catalyst and gas within the separation vessel 22 that provides an initial stage cyclonic separation. The catalyst mixture falls to the bottom of the disengaging zone 62 which defines a particle outlet for discharging fluidized catalyst particles and the vapor portion of the reaction product stream passes upwardly through a gas recovery outlet 23 for withdrawing gaseous fluids from the separation vessel 22. The vapor, comprising entrained catalyst, continues upwards to a dilute phase separator typically in the form of a series of one to three conventional cyclone separation stages shown in the drawing as 20 and 21. Cyclone separation stage 20 represents a primary cyclone separation wherein a primary cyclone vapor stream is passed to a secondary cyclone separation stage 21 and the secondary vapors from the secondary cyclone separation stage 21 are conveyed via conduit 17 to a plenum chamber 16. A net reaction product stream comprising less than about 100 ppm-wt catalyst is withdrawn via line 48 from the reactor outlet 12. Preferably, the net reaction product stream withdrawn from the fast-fluidized bed reaction zone comprises less than about 70 ppm-wt catalyst. Catalyst separated in the primary cyclone separation stage 20 drops through dip leg 59 into the bottom of the disengaging zone 62. Catalyst separated from the reaction product in the secondary cyclone separation stage falls through dip leg 60 into the bottom of the disengaging zone 62. Dip legs 59 and 60 are fitted with flapper valves (not shown) at their base to prevent the back flow of vapors through the cyclone separators. Catalyst accumulated in the bottom of the disengaging zone 62 is allowed to achieve an upper catalyst level and any excess catalyst is passed through at least one external catalyst recirculation standpipe 28 through a recirculation slide valve 32, and returned to the dense phase zone 44. Preferably, at least two external catalyst recirculation standpipes are employed to return catalyst from the disengaging zone 62 to the dense phase zone 44. Optionally, a heat transfer zone 30, such as a conventional flow-through catalyst cooler, is disposed in at least one external catalyst recirculation standpipe at a point above the recirculation slide valve 32. The use of the catalyst cooler allows the recovery and removal of excess heat from the exothermic reactions taking place in the reaction zone. Heat is typically removed from the catalyst to produce steam which can be used elsewhere in the complex. As the reaction proceeds, the activity of the catalyst in the reaction zone gradually is reduced by the buildup of coke on the catalyst. To maintain the conversion and selectivity of the reaction at acceptable levels, a portion of the catalyst mixture is withdrawn as a spent catalyst stream from the upper disengaging zone 62 and passed through a spent catalyst standpipe 42. In the spent catalyst standpipe 42, the spent catalyst stream is stripped with a stripping medium such as steam introduced in line 37 to produce a stripped catalyst stream 56. The spent catalyst standpipe 42 will typically include a stripping section that contains grids or baffles to improve contact between the catalyst and the stripping medium. The stripped catalyst stream is conveyed through line 38 and the spent catalyst slide valve 39. The stripped catalyst stream 56 is passed to a catalyst regeneration zone (not shown). In the catalyst regeneration zone, the spent catalyst stream is at least partially regenerated either by oxidation or reduction to produce a regenerated catalyst stream. Such regeneration schemes are well known to those skilled in the art of fluidized bed reaction systems. A regenerated catalyst stream 52 is returned to the lower reaction zone via a regenerated catalyst standpipe comprising line 40, regenerated catalyst slide valve 41, and line 36 to a point above the dense phase zone 44. The regenerated catalyst return is shown at a point above the dense phase zone. The return of the regenerated catalyst to the reaction zone may be provided at any point in the riser or in the upper catalyst bed. Preferably, the dense phase zone is operated to maintain a bed height of between about 2 meters (7 feet) and about 6 meters (20 feet) above the feed distributor 34 and below the intermediate portion of the reaction zone in the dense phase zone. More preferably, the bed height of the dense phase zone comprises between about 2.4 meters (8 feet) and about 4 meters (13 feet). By maintaining this bed height in the dense phase zone 44, it is believed that feedstock flow variations and "jet penetration" at the feed distributor are minimized to provide a well-mixed reaction zone comprising catalyst having a carbon content of between about 3 and 20 weight percent. It is believed that returning the regenerated catalyst to the point above the dense phase zone 44 improves the selectivity of the overall reaction toward ethylene and propylene. Freshly regenerated catalyst has the potential to crack the oxygenate feedstock to produce unwanted by-products. By contacting the feedstock with a partially regenerated catalyst in the dense phase zone and contacting the reaction products and unreacted material in the transition zone with a catalyst mixture which is a relatively more active catalyst mixture, the combination of spent catalyst with freshly regenerated catalyst, more complete conversion to the desired light olefin products is achieved.

EXAMPLE

An engineering simulation was used to develop a comparison of the present invention to the conventional bubbling bed reactor system to illustrate the advantages of the present invention. The engineering simulation is based on pilot plant operation of a fluidized bed reaction system for both a bubbling bed and a combination of the dense phase and transition phase zones of the present invention. The comparison is based on a conventional bubbling bed reactor system for the production of 120,000 metric tonnes per annum of high purity ethylene product. The operation of this conventional bubbling bed reactor system is compared to the fast-fluidized bed reactor system of the present invention as depicted in the drawing and as described hereinabove. The bubbling bed reactor comprises a lower reaction zone to contain the actual bubbling bed of fluidized catalyst and a disengaging zone which contains a three-stage cyclone separation system to remove catalyst particles from the products of the reaction. Conventional catalyst coolers are employed within the bubbling bed to remove heat from the exothermic reaction. The fast-fluidized reactor comprises a lower reaction zone containing the dense phases zone, a disengaging zone comprising at least a portion of the transition phase zone, a separation zone, and two-stages of cyclone separation. The engineering and economic advantage of the fast-fluidized reactor system over the conventional bubbling bed reactor system is illustrated in the following Table.

TABLE

Reactor Size Comparison

|  | Bubbling Bed | Fast-Fluidized Bed |
| --- | --- | --- |
| Lower Reactor Diameter, m (ft) | 9.1 (30) | 5.2 (17) |
| Upper Reactor Diameter, m (ft) | 11 (36) | 7.9 (26) |
| Catalyst Reactor Inventory, m tonnes | 114 | 44 |

As shown in the above Table, the diameter of the lower reaction zone of the fast-fluidized bed reactor is almost half of the diameter of the lower reaction zone of the conventional bubbling bed reactor. The diameter of the disengaging zone of the fast-fluidized bed reactor is 28 percent less than the diameter of the disengaging zone of the conventional bubbling bed reactor as a result of the use of the catalyst separation zone and the two-stage cyclone separation in the fast-fluidized bed reactor compared to the use of the conventional three-stage cyclone separation arrangement of the bubbling bed reactor system. Thus, the fast-fluidized bed reaction zone offers significant size and cost savings over the traditional bubbling bed reactor system and offers an almost 250 percent decrease in total reactor catalyst inventory.

I claim:

1. A process for the conversion of a feedstream comprising an oxygenate to produce light olefins, said process comprising:

a) passing said feedstream in the presence of a diluent to a dense phase zone in a lower reaction zone of a fast-fluidized bed reactor containing a fluidized non-zeolitic catalyst, and at least at effective conditions partially converting said feedstream to a product stream comprising light olefins and deactivating at least a portion of said catalyst to produce a spent catalyst having a carbonaceous deposit thereon;

b) passing said product stream, an unconverted portion of the feedstream, and a catalyst mixture comprising spent catalyst and a regenerated catalyst to a transition phase zone at a superficial velocity of greater than or equal to 2 meters per second located in said lower reaction zone above said dense phase zone wherein the unconverted portion of the feedstream is essentially completely converted to produce a transition zone effluent comprising light olefins and the catalyst mixture;

c) passing the transition zone effluent to a first separation zone in an upper disengaging zone of said reaction zone to separate a first portion of the catalyst mixture and to provide a first separated product stream and passing the first portion of the catalyst mixture to an upper catalyst bed in the upper disengaging zone;

d) passing the first separated product stream to a second separation zone to provide a net product stream comprising a reduced amount of the catalyst mixture and returning a second portion of the catalyst mixture to the upper catalyst bed;

e) returning at least a portion of the catalyst mixture from the upper catalyst bed to the dense phase zone; and f) withdrawing a third portion of the catalyst mixture from the upper catalyst bed, at least partially regenerating the third portion of the catalyst mixture to provide a regenerated catalyst, and returning the regenerated catalyst to the lower reaction zone at a point above the dense phase zone to decrease catalyst inventory.

2. The process of claim 1 wherein the light olefins comprise olefins having 2 to 4 carbon atoms per molecule.

3. The process of claim 1 wherein the non-zeolitic catalyst comprises a silicoaluminophosphate catalyst.

4. The process of claim 1 wherein the catalyst is selected from the group consisting of SAPO-34, SAPO-17, and mixtures thereof.

5. The process of claim 1 wherein the dense phase zone comprises a bed height of about 2 meters to about 4 meters.

6. The process of claim 1 further comprising cooling the catalyst mixture of step (e) prior to returning the catalyst mixture to the dense phase zone.

7. The process of claim 1 wherein the effective conditions for converting the feedstock in the dense phase include a superficial velocity of less than 2 meters per second.

8. The process of claim 1 wherein the oxygenate is selected from the group consisting of methanol, ethanol, propanol, dimethyl ether, and mixtures thereof.

9. The process of claim 1 wherein said separation comprises about one to about three cyclone separation stages.

10. The process of claim 1 further comprising lifting the regenerated catalyst to the reaction zone with a portion of the net product stream.

11. The process of claim 10 wherein the portion of the net product stream used to lift the regenerated catalyst comprises butylene.

12. The process of claim 1 further comprising passing the net product stream to a product fractionation zone to separate the net product stream into an ethylene stream, a propylene stream, and a butylene stream.

13. The process of claim 1 wherein at least one catalyst recirculation standpipe is provided to return a portion of the catalyst mixture from the upper catalyst bed to the dense phase zone.

14. The process of claim 13 wherein said recirculation standpipe comprises a catalyst cooler to cool the catalyst mixture prior to returning the catalyst mixture to the dense phase zone.

15. The process of claim 13 wherein the process comprises three recirculation standpipes and at least one of the recirculation standpipes includes a catalyst cooler.

* * * * *